United States Patent
Brito De La Fuente et al.

(10) Patent No.: US 11,272,728 B2
(45) Date of Patent: Mar. 15, 2022

(54) HIGH PROTEIN ENTERAL TUBE FEED FOR ICU PATIENTS

(71) Applicant: FRESENIUS KABI DEUTSCHLAND GMBH, Bad Homburg (DE)

(72) Inventors: Edmundo Brito De La Fuente, Friedrichsdorf (DE); Susanne Keim, Bad Homburg (DE); Ericka Pestana, Frankfurt am Main (DE)

(73) Assignee: FRESENIUS KABI DEUTSCHLAND GMBH, Bad Homburg (DE)

( * ) Notice: Subject to any disclaimer, the term of this patent is extended or adjusted under 35 U.S.C. 154(b) by 285 days.

(21) Appl. No.: 15/779,376

(22) PCT Filed: Nov. 29, 2016

(86) PCT No.: PCT/EP2016/079074
§ 371 (c)(1),
(2) Date: May 25, 2018

(87) PCT Pub. No.: WO2017/093217
PCT Pub. Date: Jun. 8, 2017

(65) Prior Publication Data
US 2018/0343912 A1 Dec. 6, 2018

(30) Foreign Application Priority Data
Nov. 30, 2015 (EP) .................... 15197108

(51) Int. Cl.
*A23L 33/00* (2016.01)
*A23L 33/17* (2016.01)
*A23L 33/10* (2016.01)
*A61J 15/00* (2006.01)
*A61K 38/00* (2006.01)

(52) U.S. Cl.
CPC ............... *A23L 33/40* (2016.08); *A23L 33/10* (2016.08); *A23L 33/17* (2016.08); *A23V 2002/00* (2013.01); *A61J 15/00* (2013.01); *A61K 38/00* (2013.01); *A61M 2202/0482* (2013.01)

(58) Field of Classification Search
CPC ..... A23L 33/40; A23L 33/17; A23V 2002/00; A61K 38/00; A61M 2202/0482
USPC ...................................... 426/61, 72
See application file for complete search history.

(56) References Cited

U.S. PATENT DOCUMENTS 9,011,935 B2 * 4/2015 Allaker ............ A61P 11/00
424/718
2011/0081400 A1 * 4/2011 Langford ............ A23L 33/15
424/439

OTHER PUBLICATIONS

Abbott Product Information-High protein, Low Fat Therapeutic Nutrition (Year: 2015).*

* cited by examiner

*Primary Examiner* — Hamid R Badr
(74) *Attorney, Agent, or Firm* — Hylton-Rodic Law PLLC

(57) ABSTRACT

Enteral tube feed for patients in an intensive care unit comprising a lipid component, a carbohydrate component and at least 30 EN % of a protein component based on the total energy content of the enteral tube feed, wherein the protein component comprises a peptide fraction consisting of di-, tri- and oligopeptides with a molecular weight of at most 1 kD, wherein the peptide fraction provides at least 10 EN % of the total energy content of the enteral composition and wherein the carbohydrate component predominantly consists of carbohydrates having a GI of ≤35 such as isomaltulose for use in treatment of ICU patients.

20 Claims, No Drawings

HIGH PROTEIN ENTERAL TUBE FEED FOR ICU PATIENTS

CROSS REFERENCE TO RELATED APPLICATIONS

This application is a U.S. national stage application of International Application No. PCT/EP2016/079074, filed Nov. 29, 2016, which claims the benefit of the filing date of European Application No. 15197108.2, Nov. 30, 2015, the contents of which are hereby incorporated by reference in their entirety.

FIELD OF THE INVENTION

The present disclosure relates to enteral tube feeds of high protein density that are sufficiently tolerable to provide high amounts of protein and other required nutrients to ICU patients. The enteral tube feeds herein comprise a protein component, a lipid component, a carbohydrate component and, preferably, vitamins and minerals (to be nutritionally complete). The present disclosure further relates to the use of such enteral tube feeds in the treatment of ICU patients.

BACKGROUND OF THE INVENTION

In the Intensive Care Unit (ICU), there is a general need for enteral tube feeds providing a high amount of protein with a relatively small volume of formula as well as with a comparably low amount of calories, in particular from lipids.

Such enteral tube feeds should be particularly well tolerated by the stressed digestive system of ICU patients. As this condition is not sufficiently fulfilled by state of the art tube feeds, it is often recommended to use trophic feeding ("underfeed") patients for the first hours/days after admission to the ICU. Also, even though there is accumulating evidence, that in general enteral feeding is superior to parenteral feeding in terms of clinical outcome, often parenteral nutrition instead of enteral nutrition is provided in order to avoid digestibility issues or aspiration.

Reoccurring issues with nutritionally complete high protein enteral tube feeds are lack of stability and high viscosities of the resulting emulsions. This behaviour is particularly pronounced in the presence of minerals which are required to provide a nutritionally complete formula. A solution may be to provide a set of enteral modules in order to separately provide protein and minerals.

However, in the ICU, patient handling and monitoring is complex enough already without having a patient specific nutrient protocol requiring application of different tube feed modules. Thus a complex nutritional system is likely to result in low compliance, in particular in view of the fact that no feeding or trophic feeding is an accepted practice in particular in the first hours/days of the ICU stay.

Moreover, for being suitable to be safely administered to an ICU patient, enteral tube feeds need to be sufficiently sterile. Thus, it is desirable that they are stable against heat sterilization, preferably repeated heat sterilization.

Accordingly, there is a need for enteral tube feeds providing a high protein density and being sufficiently tolerable to the stressed digestive system of the ICU patient. In particular there is a need for such a composition being additionally adaptable towards being nutritionally complete. Moreover, such enteral tube feeds should provide high amounts of protein with a low volume of formula and low amounts of calories.

SUMMARY OF THE INVENTION

The inventors found that, despite e.g. their high protein density, the compositions of the present disclosure are stable emulsions that can be repeatedly sterilized and are well tolerated by ICU patients.

These properties together enable the initiation of enteral feeding as early as possible after admission to the ICU in order to reach a target protein intake faster than with conventional enteral tube feeds (e.g. having a protein density of about 15-25 EN %).

This high tolerability is believed to be related to the use of a defined protein hydrolysate in combination with low GI carbohydrates and a lipid component that preferably is high in MCT. Tolerability may further be improved by relatively low amounts of energy delivered by the lipid component.

Accordingly, in a first aspect the present invention relates to an enteral tube feed for ICU patients.

In a second aspect the present invention relates to an enteral tube feed comprising a lipid component, a carbohydrate component and at least 30 EN % of a protein component based on the total energy content of the enteral tube feed, wherein the protein component comprises a peptide fraction consisting of di-, tri- and oligopeptides with a molecular weight of at most 1 kD, wherein the peptide fraction provides at least 10 EN %, preferably at least 15 EN %, more preferably at least 20 EN % of the total energy content of the enteral tube feed and wherein the carbohydrate component predominantly consists of carbohydrates having a GI of $\leq 35$, preferably $\leq 32$; more preferably disaccharides having a GI of $\leq 35$, preferably $\leq 32$; most preferred isomaltulose.

In a third aspect, the present invention relates to an enteral tube feed for ICU patients comprising at most 30 EN % of a lipid component.

In a fourth aspect, the present invention relates to a process for making such a composition.

In a fifth aspect, the present invention relates to such an enteral tube feed that is stable against repeated sterilization under heat.

In a sixth aspect, the present invention relates to a dosage regime for administration to an ICU patient, wherein the administration is started no later than 48 hours after admission to the ICU, preferably no later than 24 hours, preferably no later than 12 hours, most preferred within the first 1-6 hours after admission to the ICU.

In a seventh aspect, the present invention relates to the enteral tube feed of the present invention for use in improving the clinical outcome in ICU patients.

DETAILED DESCRIPTION OF THE INVENTION

Definitions

"High protein" as used herein refers to nutritional compositions wherein the protein component provides at least 30 EN %, of the total energy of the nutritional composition. In preferred embodiments, such nutritional compositions comprise 8-12 wt %, preferably 10-12 wt % of protein based in the total weight of the enteral tube feed. According to the present disclosure, there will typically be an upper limit to protein content such as at most 40 EN %, preferably at most 35 EN %

"Caloric density", or energy density as used herein refers to the amounts of calories provided per volume of enteral tube feed as applied to the patient/in ready to use form. The enteral tube feeds herein have a caloric density of between 0.8-1.5 kcal/mL, preferably 0.9-1.4 kcal/ml, more preferably between 1.1-1.3 kcal/ml, for example 1.2 kcal/mL.

"Ready-to-use" refers to the final form of the enteral tube feed as administered to a patient. Typically, the enteral tube feed herein are pre-packed in a ready to use format. I.e. sold in separately packed dose units that do not require any further dilution etc.

"Enteral tube feeding" refers to the delivery of nutrition (enteral tube feed) directly into the gut via a tube. The tube is usually placed into the stomach, duodenum or jejunum via either the nose, mouth or the direct percutaneous route.

"Enteral tube feed" herein refers to a synthetically produced tube feed composition. Enteral tube feeds as used herein typically are provided in liquid form. Thus, enteral tube feeds are artificial products produced by mixing/dissolving bulk ingredients in order to have a controllable nutrient profile whereby said ingredients are typically provided in solid form (e.g. powders) or liquid from (e.g. oils). The term "enteral tube feed" as used herein excludes traditional food that is e.g. purred and/or diluted.

"Nutritionally complete" refers to enteral tube feeds suitable as sole source of nutrition. Nutritionally complete enteral tube feeds comprise at least a protein component, a lipid component, a carbohydrate component, vitamins and minerals. The nutrient requirements with respect to minerals and vitamins, are known to the skilled artisan and can be found in standard nutritional guidelines such as EU commission directive 1999/21/EC (see Table 1 copied herein). Suitable nutrients according to the present disclosure fulfil the requirements of/are listed in regulation (EU) No 609/2013.

A composition "consisting of" a number of ingredients or components is to be understood as comprising no other than the named ingredients or components. In case ranges for amounts of ingredients or components are given, the individual amount of all ingredients or components within the composition has of course also to be adapted such that the sum of all amounts of all present ingredients or components adds up to 100 wt %.

"UHT-treatment" as used herein aims at killing of microorganisms. UHT treatment may be carried out with a first homogenization step with a pressure of 200-550 bar followed by UHT at 138° C.-143° C. for 6-10 seconds.

"Malnutrition" as used herein refers to one or both of Option I: body mass index (BMI, kg/m2)<18.5; Option II: the combined finding of unintentional weight loss (mandatory) and at least one of either reduced BMI or a low fat free mass index (FFMI). Weight loss is defined as either >10% of habitual weight indefinite of time, or >5% over 3 months. Reduced BMI is <20 or <22 kg/m2 in subjects younger and older than 70 years, respectively. Low FFMI is <15 and <17 kg/m2 in females and males, respectively.

An ICU patient as used herein refers to a patient admitted to an intensive care unit. An intensive care unit (ICU), also known as an intensive therapy unit or intensive treatment unit (ITU) or critical care unit (CCU), is a special department of a hospital or health care facility that provides intensive care medicine. Intensive care patients are patients with severe and life-threatening illnesses and injuries, which require constant, close monitoring and support from specialist equipment and medications in order to ensure normal bodily function. ICU's are typically distinguished from normal hospital wards by a higher staff-to-patient ratio and access to advanced medical resources and equipment that is not routinely available elsewhere. Common conditions that are treated within ICUs include ARDS (acute respiratory distress syndrome), trauma, multiple organ failure and sepsis. Patients may be transferred directly to an intensive care unit from an emergency department if required, or from a ward if they rapidly deteriorate, or immediately after surgery if the surgery is very invasive and the patient is at high risk of complications. Herein, ICU patients are preferably mechanically ventilated ICU patients.

Enteral Tube Feeds

The enteral tube feeds herein comprise nutrients in predetermined and controllable amounts. An enteral tube feed according to the present disclosure comprises a protein component, a lipid component, a carbohydrate component, and, preferably minerals and vitamins. Optionally, such a nutritional composition may further comprise dietary fibres and/or further ingredients known as food additives.

The enteral tube feed herein is liquid and will be provided as an oil-in-water emulsion (O/W).

The enteral tube feed will be adapted to have a high protein density of at least 30 EN % based on the total energy content of the enteral tube feed.

Typically, the enteral tube feed will have a density of between 0.8-1.5 kcal/mL, preferably 0.9-1.4 kcal/ml, more preferably between 1.1-1.3 kcal/ml, for example 1.2 kcal/m L.

The enteral tube feed herein comprises a lipid component, a protein component, a carbohydrate component, wherein
   a. the protein component provides at least 30 EN % of the total energy of the composition
   b. the lipid component provides at most 30 EN % of the total energy of the composition;
   c. the carbohydrate component provides at least 20 EN %, preferably at least 30 EN %, more preferred at least 40 EN %, of the total energy of the composition;

Preferably, the enteral tube feed according to the present disclosure comprises a lipid component, a protein component, a carbohydrate component, wherein
   a. the protein component provides 30-40 EN %, preferably 30-35 EN %, more preferably 32-34 EN %;
   b. the lipid component provides 20-30 EN %, preferably 22-25 EN %; and
   c. the carbohydrate component provides 30-50 EN % preferably 35-45 EN %, more preferably 40-44 EN %.

In preferred embodiments, the amount of water comprised in the present composition represents 70-90 vol %, preferably 75-85 vol % based on the total volume of the enteral tube feed (ready to use).

The enteral tube feed will typically have an osmolarity of 500-700, preferably of 550-650 mosmol/L.

Protein Component

The protein component herein comprises hydrolysed protein.

The protein component preferably comprises a peptide fraction consisting of di-, tri- and oligopeptides with a molecular weight of at most 1 kD, wherein the peptide fraction provides at least 10 EN %, preferably at least 15 EN %, more preferably at least 20 EN % of the total energy content of the enteral composition.

Such a protein component is believed to improve tolerability, promote gastric emptying, decrease gastroesophageal reflux and thereby reduce the probability for aspiration, in particular in mechanically ventilated ICU patients. Moreover, such a protein component supports stability of the enteral tube feed and improves its viscosity, in particular in combination with minerals, thereby providing for a liquid product that can be administered by a tube with small diameter.

In preferred embodiments, the protein component comprises hydrolysed whey protein, even more preferably, the protein component consists of hydrolysed whey protein.

The enteral tube feed herein typically comprises at least 8-15 wt %, preferably at least 9-12 wt %, even more preferably 10-12 wt % of protein, such as e.g. 10 wt % of protein based on the total weight of the enteral tube feed.

In preferred embodiments, the protein component provides at least 30-40 EN %, preferably 30-35 EN %, more preferably 32-34 EN % based on the total energy of the enteral tube feed.

Preferably, the protein to water ratio of the present nutritional composition is between 1.0/10 [g/g] and 1.5/10 [g/g], preferably 1.2/10 [g/g] and 1.3/10 [g/g], such as e.g. 1.25/10 [g/g].

Carbohydrate Component

The carbohydrate component may comprise one or more carbohydrate sources. The carbohydrate component predominantly consists of carbohydrates with low glycemic index (GI), such as a GI of ≤35, preferably ≤32; more preferably disaccharides with a GI of ≤35, preferably ≤32; most preferably isomaltulose. With respect to the carbohydrate component herein, "predominantly" refers to presence of at least 50 wt %, preferably at least 55 wt %, more preferably at least 60 wt % based on the total weight of the carbohydrate component.

The carbohydrate component typically provides at least 20 EN %, preferably at least 30 EN %, more preferred at least 40 EN %, based on the total energy of the enteral tube feed.

Preferably, the carbohydrate component provides 30-50 EN % preferably 35-45 EN %, more preferably 40-44 EN % based on the total energy of the enteral tube feed.

Fibre

The nutritional composition herein may comprise ingredients declarable as dietary fibres. Suitable dietary fibres may be included in the carbohydrate component and may be selected from the group consisting of cocoa powder, inulin, wheat dextrine, cellulose, microcrystalline cellulose, soy polysaccharides, tapioca dextrine, xanthan, fructooligosaccharides, galactooligosaccharides, at least partially hydrolysed guar gum, acacia gum, pectin, oat fibre, poly dextrose, resistant starch, hemicellulose and mixtures thereof.

A preferred fibre mixture consists of 80-99 wt %, preferably 90-96 wt % of soluble dietary fibre and 1-20 wt %, preferably 4-10 wt % of insoluble dietary fibre each based on the total weight of dietary fibre.

The fibre mixture may consist of 80-99 wt %, preferably 85-95 wt % of fermentable dietary fibre and 1-20 wt %, preferably 5-15 wt % of non-fermentable dietary fibre each based on the total weight of dietary fibre.

The fibre mixture may comprise or consist of tapioca dextrin and cellulose.

Preferably, the enteral tube feed comprises between 0.1 and 2.0 wt %, preferably 0.5 to 1.0 wt % of dietary fibre, such as the fibre mixture described hereinabove, based on the total weight of the enteral tube feed.

Lipid Component

The lipid component may comprise one or more lipid sources, such as lipids of animal and/or vegetable origin.

The lipid component of the enteral tube feed is specifically adapted to the needs of ICU patients. It is consciously designed to prevent/reduce lipid overfeeding and to improve tolerability. At the same time, the lipid component herein is designed to counteract inflammatory processes, which ICU patients are at particular risk of.

With its relatively low amount of lipids, the tube feed is specifically adapted to the needs of ICU patients. ICU patients are typically heavily medicated inter alia with drugs provided in lipid emulsions, such as certain sedating drugs. Typical examples are propofol lipid emulsions. Moreover, such drugs are often provided by constant infusion.

Therefore, standard medical treatment in the ICU typically requires administration of a non-negligible amount of calories resulting from drugs applied as lipid emulsions. Often the need for such drug lipid emulsions is highest within the first few days after admission to the ICU.

However, overfeeding of ICU patients, in particular lipid overfeeding, can result in serious side effects, hyperlipidaemia being just one example.

Accordingly, standard enteral feeds, that typically have an energy contribution of the lipid component of at least 30 EN % and at the same time provide no more than 25 EN % of protein, each based on the total energy content of said standard enteral feed, are not ideal for ICU patients, in particular when higher doses of protein should be applied as early as possible after admission to the ICU.

Therefore, while providing at least 30 EN % of protein, the enteral tube feed of the present disclosure preferably comprises less than 30 EN % of lipids based on the total energy content of the enteral tube feed.

In general, for the present enteral tube feed, less than 5 wt %, e.g. 2-4 wt % of the total weight of the composition may be provided by the lipid component.

The lipid component comprises medium chain triglycerides (MCT), for example in form of an MCT-oil. MCT herein refers to triglycerides of fatty acids with a chain length of 6-12 carbon atoms (C6-C14), preferably C6, C8, C10, C12 and C14.

Preferably, MCT are a major lipid source. Accordingly, the lipid component may comprise at least 30 wt % of MCT, preferably, at least 35 wt %, for example 40 wt % of MCT based on the total weight of the lipid component. The MCT may be present in amounts of 30-50 wt %, 35-45 wt %, such as 37-43 wt % based on the total weight of the lipid component.

In terms of energy contribution, the MCT may provide 8-12 EN % based on the total energy of the enteral tube feed.

In addition to MCT, the lipid component may comprise long chain fatty acids, preferably in the form of triglycerides comprising saturated (SFA), mono-unsaturated (MUFA) and polyunsaturated fatty acids (PUFA).

The SFA may provide 2-3 EN % based on the total energy content of the enteral tube feed.

The MUFA may provide 4-8 EN % based on the total energy content of the enteral tube feed.

The PUFA may provide 4-8 EN % based on the total energy content of the enteral tube feed.

The PUFA may comprise linoleic acid, alpha linolenic acid, EPA and DHA.

In the lipid component, the ratio of n6/n3 PUFA (g/g) may be between 0.4-0.6.

For example, in addition to the MCT-oil, the lipid component may comprise an oil of marine origin, such as fish oil and oil from plant origin, such as rapeseed-oil.

The marine oil may be provided by fish oil.

The vegetable oil may be provided by rapeseed oil.

Therefore, in one embodiment the lipid component consists of a mixture of MCT oil, fish oil and rapeseed oil.

Vitamins and Minerals

To be regarded as nutritionally complete, nutritional compositions have to comprise vitamins and minerals in addition to the protein, lipid and carbohydrate components.

Suitable vitamins to be included in the composition in order to render it nutritionally complete according to the present disclosure are Vitamin A, Vitamin D, Vitamin K, Vitamin C, Thiamin, Riboflavin, Vitamin B6, Niacin, Folic acid, Vitamin B12, Pantothenic acid, Biotin and Vitamin E. An example for rendering a nutritional composition complete in vitamins is given in table 1.

Suitable minerals to be included in the composition in order to render it nutritionally complete according to the present disclosure are Sodium, Chloride, Potassium, Calcium, Phosphorus, Magnesium, Iron, Zinc, Copper, Iodine, Selenium, Manganese, Chromium and Molybdenum. Optionally, Fluoride may be included. An example for rendering a nutritional composition complete in minerals is given in table 1.

Additives

Nutritional compositions optionally comprise food additives. Additives are typically present in total amounts of less than 10 wt %, 5 wt % or even less than 1 wt % based on the total weight of the nutritional composition. Exemplary additives are choline, beta-carotene, lutein, lycopene, caffeine, lecithin, taurine, carnitine, myo-inositol, colorants, aroma and mixtures thereof. Aromas may be caramel, vanilla, yoghurt, chocolate, coffee, cappuccino, fruit aromas and the like.

The additives may include stabilisers and emulsifiers. Preferably, the stabilisers are selected from microcrystalline cellulose E460 and Sodium Carboxymethylcellulose E466 (preferably used in combination) and the emulsifiers are selected from mono-diglycerides such as citric acid ester of mono-diglyceride E472c.

Use in Treatment of ICU Patients

The enteral tube feed of the present disclosure may be used in therapeutic treatment of ICU patients.

The enteral tube feed may be used in prevention and treatment of malnutrition, cachexia or protein depletion of ICU patients.

The enteral tube feed may be used in prevention of aspiration in ICU patients, preferably in mechanically ventilated ICU patients.

The enteral tube feed may be used in prevention and treatment of hyperlipidaemia in ICU patients, preferably in ICU patients requiring drugs provided in from of lipid emulsions.

For example, the enteral tube feed may be used in prevention and treatment of hyperlipidaemia in ICU patients receiving propofol in form of lipid emulsions and/or (supplemental) parenteral nutrition in form of lipid emulsions.

The enteral tube feed may be used in prevention and treatment of malnutrition and/or protein depletion in ICU patients, preferably in ICU patients requiring drugs provided in from of lipid emulsions. For example, the enteral tube feed may be used in prevention and treatment of malnutrition and/or protein depletion in ICU patients receiving propofol in form of lipid emulsions and/or parenteral nutrition in form of lipid emulsions.

The enteral tube feed may be used for improving the clinical outcome of the ICU patients. In particular an improved clinical outcome when compared to standard enteral tube feeds. Improved clinical outcome may be reflected in a shorter ICU stay, faster start of target enteral nutrient intake, such as target protein intake, decrease in days on mechanical ventilation or even in a faster and/or better recovery from the underlying severe illness or injury having required the admission to an ICU, e.g. trauma, sepsis, stroke, infections, myocardial infarction, anaphylactic shock or intoxication. Improved clinical outcome may also be reflected by an improved (reduced) SOFA (Sequential Organ Failure Assessment) score. Preferably, improved clinical outcome is reflected by one or more of a shorter ICU stay, less days requiring mechanical ventilation and faster start of target enteral nutrient intake, such as target protein intake.

The enteral tube feed may be used to achieve a daily target protein intake of 1.0-2.0 g, preferably 1.2-1.8 g, more preferably, 1.4-1.8 g of protein per kg bodyweight as early as possible after admission to the ICU. The target protein intake is calculated relative to the admission body weight. Accordingly, the enteral tube feed may be used to achieve a daily target protein intake of 1.0-2·g, preferably 1.2-1.8 g, more preferably, 1.4-1.8 g of protein per kg bodyweight in ICU patients, preferably in ICU patients requiring drugs provided in from of lipid emulsions, e.g. in ICU patients receiving propofol in form of lipid emulsions and/or (supplemental) parenteral nutrition in form of lipid emulsions.

The enteral tube feed may be used to provide a daily dose of protein of 1.0-2·g, preferably 1.2-1.8 g, more preferably, 1.4-1.8 g of protein per kg bodyweight in ICU patients, at least in the acute phase (24 h-48 h hours after admission to an ICU)

Administration of the enteral tube feed disclosed herein is preferably started no later than 48 hours after admission to the ICU, preferably no later than 24 hours, preferably no later than 12 hours, most preferred within the first 1-6 hours after admission to the ICU.

Daily Dose and Dose Unit

An average daily dose based on the needs of an ICU patient of average weight is described below.

The enteral tube feed of the present disclosure may provide an average daily dose of 1000-1400 kcal.

The enteral tube feed of the present disclosure may provide an average daily dose of 80-120 g of the protein component.

The enteral tube feed of the present disclosure may provide an average daily dose of 30-35 g of the lipid component.

The enteral tube feed of the present disclosure may provide an average daily dose of 110-150 g of the carbohydrate component.

The enteral tube feed of the present disclosure may provide an average daily dose of 3-10 g dietary fibre.

The enteral tube herein may be adapted to provide 20-25 kcal/kg BW/day in the acute phase (24 h-48 h hours after admission to an ICU) and an increased daily dose of calories of 25-30 kcal/kg BW/day in the stabilized patient (>48 hours after admission to the ICU).

For ease of use and in order to increase compliance, the average daily dose may be provided in packages (dose units). Preferably, the average daily dose is provided in one or two packages (dose units).

The average daily dose may be provided in a single dose unit, for example the average daily dose may be provided in a single tube feed package, such as a tube feed package comprising 800-1200 mL of the enteral tube feed disclosed herein. Preferably, the average daily dose may be provided in two dose units wherein each provides half of the average daily dose unit, e.g. for an average bodyweight of 70 kg or 75 kg. For example, half of the average daily dose may be provided in a single tube feed package, such as a tube feed package comprising 400-600 mL of the enteral tube feed disclosed herein.

Process

The enteral tube feed herein is obtainable by the following process.

In a first step, the protein is mixed with water, the water may optionally be premixed with other ingredients in powder form.

In a second step, ingredients in oil form are added to and mixed with the mixture obtained by the first step.

In a third step, the mixture obtained by the second step is homogenized at 200-550 bar.

In a fourth step, the mixture obtained by the third step is subjected to UHT treatment, preferably at 138-143° C. for 6-10 seconds. The fourth step optionally includes an aseptic homogenization at 100-300 bar after the UHT treatment.

In a fifth step, the mixture obtained in the fourth step is filled into a package holding a dose unit and the package is sealed. Optionally, this step may be carried out under aseptic conditions.

In an optional sixth step, the package obtained in the fifth step may be subjected to a further sterilization at 116-121° C. for 1-20 minutes.

EXEMPLARY EMBODIMENTS

Embodiment 1

Enteral tube feed comprising a lipid component, a carbohydrate component and
at least 30 EN % of a protein component based on the total energy content of the enteral tube feed,
wherein the protein component comprises a peptide fraction consisting of di-, tri- and oligopeptides with a molecular weight of at most 1 kD,
wherein the peptide fraction provides at least 10 EN %, preferably at least 15 EN %, more preferably at least 20 EN % of the total energy content of the enteral composition and
wherein the carbohydrate component predominantly consists of carbohydrates having a GI of ≤35, preferably ≤32; more preferably disaccharides having a GI of ≤35, preferably ≤32; most preferably isomaltulose for use in (nutritional) treatment of ICU patients.

Embodiment 2

Enteral tube feed for use according to embodiment 1 in treatment and prevention of malnutrition, preferably protein malnutrition in ICU patients.

Embodiment 3

Enteral tube feed for use according to any of the preceding embodiments, wherein the enteral tube feed comprises at least 8-15 wt %, preferably at least 9-12 wt %, even more preferably 10-12 wt % of protein, such as e.g. 10 wt % of protein based on the total weight of the enteral tube feed.

Embodiment 4

Enteral tube feed for use according to any of the preceding embodiments, wherein the administration is started no later than 48 hours after admission to the ICU, preferably no later than 24 hours, preferably no later than 12 hours, most preferred within the first 1-6 hours after admission to the ICU.

Embodiment 5

Enteral tube feed for use according to any of the preceding embodiments, wherein the use is further specified in providing a daily dose of calories of 20-25 kcal/kg BW/day in the acute phase (24 h-48 h hours after admission to an ICU) and an increased daily dose of calories of 25-30 kcal/kg BW/day in the stabilized patient (>48 hours after admission to the ICU).

Embodiment 6

Enteral tube feed for use according to any of the preceding embodiments, wherein the use is further specified in providing a daily dose of protein of at least 1.0 g/kg BW/day, preferably at least 1.2 g/kg BW/day, more preferably at least 1.4 g/kg BW/day at least in the acute phase (24 h-48 h hours after admission to an ICU).

Embodiment 7

Enteral tube feed comprising a lipid component, a carbohydrate component and at least 30 EN % of a protein component based on the total energy content of the enteral tube feed, wherein the protein component comprises a peptide fraction consisting of di-, tri- and oligopeptides with a molecular weight of at most 1 kD, wherein the peptide fraction provides at least 10 EN %, preferably at least 15 EN %, more preferably at least 20 EN % of the total energy content of the enteral tube feed and wherein the carbohydrate component predominantly consists of carbohydrates having a GI of ≤35, preferably ≤32, more preferably disaccharides having a GI of ≤35, preferably ≤32, most preferably isomaltulose.

Embodiment 8

Enteral tube feed according to any of the preceding embodiments, wherein the lipid component provides at most 35 EN %, preferably 30 EN % based on the total energy content of the enteral tube feed.

Embodiment 9

Enteral tube feed according to any of the preceding embodiments, wherein the lipid component comprises at least 30 wt %, preferably at least 40 wt % of MCT based on the total weight of the lipid component.

Embodiment 10

Enteral tube feed according to any of the preceding embodiments, wherein the lipid component comprises 30-50 wt % MCT oil, 20-40 wt % fish oil and 20-40 wt % vegetable oil.

Embodiment 11

Enteral tube feed according to any of the preceding embodiments, wherein the carbohydrate component comprises at least 50 wt % of carbohydrates having a GI of at most 32, preferably disaccharides having a GI of ≤35, preferably ≤32, more preferably isomaltulose, 5-20 wt % of starch and 20-40 wt % of further oligo- and polysaccharides.

Embodiment 12

Enteral tube feed according to any of the preceding embodiments wherein the lipid component comprises 15-35 EN %, the carbohydrate component comprises 30-50 EN % and the protein component comprises 30-40 EN % each based on the total energy content of the enteral tube feed.

Embodiment 13

Enteral tube feed according to any of the proceeding embodiments having an energy density of 1.0-2.0 kcal/mL, preferably up to 1.5 kcal/mL, more preferably 1.1-1.4 kcal/mL.

Embodiment 14

Enteral tube feed according to any of the preceding embodiments comprising 75-85 ml water/100 mL.

Embodiment 15

The enteral tube feed of any of the preceding embodiments comprising a fibre mixture consisting of 80-99 wt %, preferably 90-96 wt % of soluble dietary fibre and 1-20 wt %, preferably 4-10 wt % of insoluble dietary fibre.

Embodiment 16

The enteral tube feed of any of the preceding embodiments comprising a fibre mixture consisting of 80-99 wt %, preferably 85-95 wt % of fermentable dietary fibre and 1-20 wt %, preferably 5-15 wt % of non-fermentable dietary fibre.

Embodiment 17

The enteral tube feed of any of the preceding embodiments having an osmolarity of 500-700, preferably of 550-650 mosmol/L.

Embodiment 18

Enteral tube feed according to any of the preceding embodiments for use in improving the clinical outcome in ICU patients.

Embodiment 19

Enteral tube feed according to any of the preceding embodiments for use in improving the clinical outcome in ICU patients, wherein an improved clinical outcome is reflected in a shorter ICU stay, faster start of target enteral nutrient intake, such as target protein intake, decrease in days on mechanical ventilation, improved SOFA score, or in a faster and/or better recovery from the underlying severe illness or injury having required the admission to an ICU.

Embodiment 20

A process for making the enteral tube feed of any of the preceding embodiments comprising the following steps:
a) a first step, wherein the protein is mixed with water, the water may optionally be premixed with other ingredients in powder form;
b) a second step, wherein ingredients in oil form are added to and mixed with the mixture obtained by the first step;
c) a third step, wherein the mixture obtained by the second step is homogenized at 200-550 bar;
d) a fourth step, wherein the mixture obtained by the third step is subjected to UHT treatment, preferably at 138-143° C. for 6-10 seconds, optionally, the fourth step includes an aseptic homogenization at 100-300 bar after the UHT treatment;
e) a fifth step, wherein the mixture obtained in the fourth step is filled into a package holding a dose unit and the package is sealed, optionally, this step may be carried out under aseptic conditions;
f) an optional sixth step, wherein the package obtained in the fifth step may be subjected to a further sterilization at 116-121° C. for 1-20 minutes.

Embodiment 21

The process according to embodiment 20, wherein the water of the first step is premixed with minerals and vitamins.

Embodiment 22

Dose unit comprising all or half of the average daily dose of the enteral tube feed wherein the average daily dose comprises 1000-1400 kcal, 80-120 g of the protein component, 30-35 g of the lipid component, 110-150 g of the carbohydrate component and 3-10 g dietary fibre.

The present disclosure includes methods of treatment comprising the step of administering the enteral tube feed described herein:

Embodiment 23

Method of (nutritional) treatment of ICU patients comprising the step of administering (to said ICU patients) an enteral tube feed comprising a lipid component, a carbohydrate component and
at least 30 EN % of a protein component based on the total energy content of the enteral tube feed,
wherein the protein component comprises a peptide fraction consisting of di-, tri- and oligopeptides with a molecular weight of at most 1 kD,
wherein the peptide fraction provides at least 10 EN %, preferably at least 15 EN %, more preferably at least 20 EN % of the total energy content of the enteral composition and
wherein the carbohydrate component predominantly consists of carbohydrates having a GI of ≤35, preferably ≤32; more preferably disaccharides having a GI of ≤35, preferably ≤32; most preferably isomaltulose.

Embodiment 24

Method of (nutritional) treatment or prevention of malnutrition in ICU patients comprising the step of administering (to said ICU patients) an enteral tube feed comprising a lipid component, a carbohydrate component and
at least 30 EN % of a protein component based on the total energy content of the enteral tube feed,
wherein the protein component comprises a peptide fraction consisting of di-, tri- and oligopeptides with a molecular weight of at most 1 kD,
wherein the peptide fraction provides at least 10 EN %, preferably at least 15 EN %, more preferably at least 20 EN % of the total energy content of the enteral composition and
wherein the carbohydrate component predominantly consists of carbohydrates having a GI of ≤35, preferably ≤32; more preferably disaccharides having a GI of ≤35, preferably ≤32; most preferably isomaltulose.

Embodiment 25

Method of (nutritional) treatment or prevention of protein malnutrition in ICU patients comprising the step of administering (to said ICU patients) an enteral tube feed comprising a lipid component, a carbohydrate component and
- at least 30 EN % of a protein component based on the total energy content of the enteral tube feed,
- wherein the protein component comprises a peptide fraction consisting of di-, tri- and oligopeptides with a molecular weight of at most 1 kD,
- wherein the peptide fraction provides at least 10 EN %, preferably at least 15 EN %, more preferably at least 20 EN % of the total energy content of the enteral composition and
- wherein the carbohydrate component predominantly consists of carbohydrates having a GI of ≤35, preferably ≤32; more preferably disaccharides having a GI of ≤35, preferably ≤32; most preferably isomaltulose.

Embodiment 26

Method of treatment according to any of embodiments 23-25, wherein the enteral tube feed comprises at least 8-15 wt %, preferably at least 9-12 wt %, even more preferably 10-12 wt % of protein, such as e.g. 10 wt % of protein based on the total weight of the enteral tube feed.

Embodiment 27

Method of treatment according to any of embodiments 23-26, wherein the administration is started no later than 48 hours after admission to the ICU, preferably no later than 24 hours, preferably no later than 12 hours, most preferred within the first 1-6 hours after admission to the ICU.

Embodiment 28

Method of treatment according to any of embodiments 23-27, wherein the method is further specified in providing a daily dose of calories of 20-25 kcal/kg BW/day in the acute phase (24 h-48 h hours after admission to an ICU) and an increased daily dose of calories of 25-30 kcal/kg BW/day in the stabilized patient (>48 hours after admission to the ICU).

Embodiment 29

Method of treatment according to any of embodiments 23-28, wherein the method is further specified in providing a daily dose of protein of at least 1.0 g/kg BW/day, preferably at least 1.2 g/kg BW/day, more preferably at least 1.4 g/kg BW/day at least in the acute phase (24 h-48 h hours after admission to an ICU).

The present disclosure includes the use of the enteral tube feed described herein in the manufacture of therapeutic compositions:

Embodiment 30

Use of an enteral tube feed comprising a lipid component, a carbohydrate component and
- at least 30 EN % of a protein component based on the total energy content of the enteral tube feed,
- wherein the protein component comprises a peptide fraction consisting of di-, tri- and oligopeptides with a molecular weight of at most 1 kD,
- wherein the peptide fraction provides at least 10 EN %, preferably at least 15 EN %, more preferably at least 20 EN % of the total energy content of the enteral composition and
- wherein the carbohydrate component predominantly consists of carbohydrates having a GI of ≤35, preferably ≤32; more preferably disaccharides having a GI of ≤35, preferably ≤32; most preferably isomaltulose
for the manufacture of a therapeutic composition for (nutritional) treatment of ICU patients.

Embodiment 31

Use according to embodiment 30, wherein the therapeutic composition is for treatment and prevention of malnutrition, preferably protein malnutrition in ICU patients.

Embodiment 32

Use according to any of the preceding embodiments, wherein the enteral tube feed comprises at least 8-15 wt %, preferably at least 9-12 wt %, even more preferably 10-12 wt % of protein, such as e.g. 10 wt % of protein based on the total weight of the enteral tube feed.

Embodiment 33

Use according to any of the preceding embodiments, wherein the administration is started no later than 48 hours after admission to the ICU, preferably no later than 24 hours, preferably no later than 12 hours, most preferred within the first 1-6 hours after admission to the ICU.

Embodiment 34

Use according to any of the preceding embodiment s, wherein the use is further specified in providing a daily dose of calories of 20-25 kcal/kg BW/day in the acute phase (24 h-48 h hours after admission to an ICU) and an increased daily dose of calories of 25-30 kcal/kg BW/day in the stabilized patient (>48 hours after admission to the ICU).

Embodiment 35

Use according to any of the preceding embodiments, wherein the use is further specified in providing a daily dose of protein of at least 1.0 g/kg BW/day, preferably at least 1.2 g/kg BW/day, more preferably at least 1.4 g/kg BW/day at least in the acute phase (24 h-48 h hours after admission to an ICU).

Embodiment 36

Use according to any of embodiments 30-35, wherein the therapeutic composition is for use in improving the clinical outcome in ICU patients.

Embodiment 37

Use according to embodiment 47, wherein an improved clinical outcome is reflected in a shorter ICU stay, faster start of target enteral nutrient intake, such as target protein intake, decrease in days on mechanical ventilation, improved SOFA score, or in a faster and/or better recovery from the underlying severe illness or injury having required the admission to an ICU.

EXAMPLES

Stability Test/UHT Treatment

Sample enteral tube feeds according to the table below where prepared and subjected to UHT treatment UHT treatment was carried out with a first homogenization step with a pressure of 200-550 bar followed by UHT at 138° C.-143° C. for 6 seconds.

However, for EN test 2, UHT treatment was not possible. The UHT was blocked immediately when the product was in the UHT heating system. Therefore, EN test 2 is not suitable as enteral tube feed for providing the target protein density to ICU patients who have to receive sufficiently sterile solutions.

EN test 1 however was stable against UHT treatment.

| NUTRIENTS | | EN TEST 1 | EN TEST 2 |
|---|---|---|---|
| | | Values per | |
| | | 100 ml | 100 ml |
| Energy | kcal | 122 | 122 |
| Caloric density | kcal/ml | 1.2 | 1.2 |
| Water | ml | 80.5 | 80.5 |
| Osmolarity | mosmol/l | 600 | 600 |
| Protein | 33 Energy % g | 10.0 | 10.0 |
| thereof casein/whey | % | 100% whey protein hydrolysate | 100% whey protein consentrate (non-hydrolysed) |
| Fat thereof | 24 Energy % g | 3.2 | 3.2 |
| MCT | 9.4 Energy % g | 1.28 | 1.28 |
| LCT | | 1.92 | 1.92 |
| SFA[1)2)] | 2.8 Energy % g | 0.38 | 0.38 |
| MUFA[1)] | 6.0 Energy % g | 0.82 | 0.82 |
| PUFA[1)] | 5.3 Energy % g | 0.72 | 0.72 |
| Linoleic acid | g | 0.20 | 0.20 |
| α-Linolenic acid | g | 0.09 | 0.09 |
| EPA + DHA | g | 0.30 | 0.30 |
| n6/n3 Fatty Acids | g | 0.5 | 0.5 |
| Cholesterol | mg | ≤10 | ≤10 |
| CHO (isomaltulose) | 42 Energy % g | 12.9 | 12.9 |
| Dietary fibre thereof | 1 Energy % g | 0.64 | 0.64 |
| tapioca dextrin fibre | g | 0.60 | 0.60 |
| cellulose | g | 0.04 | 0.04 |
| soluble/insoluble | % | 94/6 | 94/6 |
| fermentable/nonfermentable | % | 91/9 | 91/9 |
| Protein | 33 Energy % g | 10.0 | 10.0 |
| thereof casein/whey | % | 100% whey protein hydrolysate | 100% whey protein (non-hydrolysed) |

Clinical study protocol for the assessment of tolerability and clinical outcome of early protein intake when using the enteral tube feed herein (enteral tube feed according to the embodiments herein e.g. EN test 1) containing high protein and low fat content (per daily dose).

Patients: Inclusion criteria: Adult critically ill ventilated patients with indication for enteral nutrition and an expected ICU stay of one week or longer. Exclusion criteria: Contraindication for enteral nutrition (gut ischemia, obstruction or perforation distal from the nutritional tube); Expected intolerance for enteral nutrition (paralytic ileus); Short bowel syndrome; Child C liver cirrhosis or acute liver failure; Dialysis dependency; Requiring other specific enteral nutrition for medical reason; BMI>35 kg/m2; Extensive treatment limitations.

Nr of patients: 20 patients receiving more than five full days of enteral nutrition with the study formula Intervention: The study formula is started within 24-h after ICU admission, as soon as the circulation has been stabilized. Stable vasopressor support is no contraindication for the start of nutrition. Nutrition is primarily administered by the gastric tube at a rate of 20 ml/h and speed of administration is increased up to target if gastric retention is 250 ml or less. When gastric retention >250 ml twice, erythromycin is added as a prokinetic. If gastric retention remains, a duodenal tube is inserted. Target protein intake: 1.2 g/kg preadmission body weight. Duration of the intervention: The study formula is administered for a maximum of 7 days, or less when the patient can eat normally, is discharged from the intensive or medium care unit to the normal ward or dies. Primary endpoint: Time to target protein intake compared to control. Secondary endpoint: Nr/% of patients with protein intake <1.0 or >1.4 g/kg/day Good tolerance is inter alia reflected by easy digestion and absorption, good gastro intestinal tolerance. The time to reach the target protein intake of 1.0, 1.1 and/or (preferred target protein intake) 1.2 g/kg preadmission body weight is recorded. Reaching of higher protein intakes is recorded as appropriate.

TABLE 2

Vitamins

| | Minimum per 100 kcal | Maximum per 100 kcal |
|---|---|---|
| Vitamin A (μg RE) | 35 | 180 |
| Vitamin D (μg) | 0.5 | 3 |
| Vitamin K (μg) | 3.5 | 20 |
| Vitamin C (mg) | 2.2 | 22 |
| Thiamin (mg) | 0.06 | 0.5 |
| Riboflavin (mg) | 0.08 | 0.5 |
| Vitamin B6 (mg) | 0.08 | 0.5 |
| Niacin (mg EN) | 0.9 | 3 |
| Folic acid (μg) | 10 | 50 |
| Vitamin B12 (μg) | 0.07 | 0.7 |
| Pantothenic acid (mg) | 0.15 | 1.5 |
| Biotin (μg) | 0.75 | 7.5 |
| Vitamin E (mg α-TE) | 0.5 | 3 |

TABLE 3

Minerals

| | Minimum per 100 kcal | Maximum per 100 kcal |
|---|---|---|
| Sodium (mg) | 30 | 175 |
| Chloride (mg) | 30 | 175 |
| Potassium (mg) | 80 | 295 |
| Calcium (mg) | 35 | 250 |
| Phosphorus (mg) | 30 | 80 |
| Magnesium (mg) | 7.5 | 25 |
| Iron (mg) | 0.5 | 2.0 |
| Zinc (mg) | 0.5 | 1.5 |
| Copper (μg) | 60 | 500 |
| Iodine (μg) | 6.5 | 35 |
| Selenium (μg) | 2.5 | 10 |
| Manganese (mg) | 0.05 | 0.5 |
| Chromium (μg) | 1.25 | 15 |
| Molybdenum (μg) | 3.5 | 18 |
| Flouride (mg) | — | 0.2 |

The invention claimed is:

1. Enteral tube feed comprising a lipid component, a carbohydrate component and at least 30 energy % (EN %) of a protein component based on the total energy content of the enteral tube feed, wherein the protein component comprises a peptide fraction consisting of di-, tri- and oligopeptides with a molecular weight of at most 1 kD, wherein the peptide fraction provides at least 10 EN % of the total energy content of the enteral composition and wherein the carbohydrate component predominantly consists of carbohydrates having a low glycemic index (GI) of ≤35.

2. The enteral tube feed according to claim 1 comprising 10-12 wt. % protein based on the total weight of the enteral tube feed.

3. An enteral tube feed comprising a lipid component, a carbohydrate component and at least 30 EN % of a protein component based on the total energy content of the enteral tube feed, wherein the protein component comprises a peptide fraction consisting of di-, tri- and oligopeptides with a molecular weight of at most 1 kD, wherein the peptide fraction provides at least 10 EN % of the total energy content of the enteral tube feed and wherein the carbohydrate component predominantly consists of carbohydrates having a GI≤32.

4. The enteral tube feed according to claim 1, wherein the lipid component provides at most 35 EN % based on the total energy content of the enteral tube feed.

5. The enteral tube feed according to claim 1, wherein the lipid component comprises at least 30 wt. % of medium chain triglycerides (MCT) based on the total weight of the lipid component.

6. The enteral tube feed according to claim 1, wherein the lipid component comprises 30-50 wt. % MCT oil, 20-40 wt % fish oil and 20-40 wt. % vegetable oil.

7. The enteral tube feed according to claim 1, wherein the carbohydrate component comprises at least 50 wt. % of carbohydrates having a GI of at most 35, 5-20 wt. % of starch and 20-40 wt. % of further oligo- and polysaccharides.

8. The enteral tube feed according to claim 1, wherein the lipid component provides 15-35 EN %, the carbohydrate component provides 30-50 EN % and the protein component provides 30-40 EN % each based on the total energy content of the enteral tube feed.

9. The enteral tube feed according to claim 1, wherein said enteral feed has an energy density of 1.0-2.0 kcal/ml, up to 1.5 kcal/ml, or 1.1-1.4 kcal/ml.

10. The enteral tube feed according to claim 1, wherein said enteral feed further comprises 75-85 ml water/100 mL.

11. The enteral tube feed according to claim 1, wherein said enteral feed further comprises a fibre mixture consisting of 80-99 wt. % of soluble dietary fibre and 1-20 wt. % of insoluble dietary fibre based on the total weight of dietary fibre.

12. The enteral tube feed according to claim 1, wherein said enteral feed further comprises a fibre mixture consisting of 80-99 wt. % of fermentable dietary fibre and 1-20 wt. % of non-fermentable dietary fibre based on the total weight of dietary fibre.

13. The enteral tube feed of claim 1, wherein said enteral feed has an osmolarity of 500-700 mosmol/L.

14. The enteral feed of claim 1, wherein the carbohydrate component consists of at least 50 wt. % isomaltulose, wherein the enteral tube feed comprises 10-12 wt. % protein based on the total weight of the enteral tube feed and wherein the enteral tube feed has an energy density of 1.1-1.4 kcal/ml.

15. A method of treating an intensive care unit (ICU) patient, said method comprising administrating to said an intensive care unit (ICU) patient an enteral tube feed comprising a lipid component, a carbohydrate component and at least 30 EN % of a protein component based on the total energy content of the enteral tube feed, wherein the protein component comprises a peptide fraction consisting of di-, tri- and oligopeptides with a molecular weight of at most 1 kD, wherein the peptide fraction provides at least 10 EN % of the total energy content of the enteral composition and wherein the carbohydrate component predominantly consists of carbohydrates having a GI of less than, or equal to, 35.

16. The method of claim 15, wherein the administration is started 48 hours or less after admission to the ICU.

17. The method of claim 15, wherein said patient is provided a daily dose of calories of 20-25 kcal/kg body weight (BW)/day in the acute phase and an increased daily dose of calories of 25-30 kcal/kg BW/day when the patient is stabilized.

18. The method of claim 15, wherein said patient is provided a daily dose of protein of at least 1.0 g/kg BW/day at least in the acute phase.

19. The method of claim 15, wherein said method comprises improving the clinical outcome in ICU patients, wherein said improved clinical outcome is reflected in a shorter ICU stay, faster start of target enteral nutrient intake, decrease in days on mechanical ventilation, improved Sequential Organ Failure Assessment (SOFA) score, or in a faster and/or better recovery from the underlying severe illness or injury having required the admission to an ICU.

20. The method of claim 15, wherein said method comprises treating and/or preventing malnutrition.

* * * * *